United States Patent [19]

Jessup et al.

[11] Patent Number: 4,629,579

[45] Date of Patent: * Dec. 16, 1986

[54] BORON DERIVATIVES

[75] Inventors: Peter J. Jessup, Santa Ana; Richard A. Holstedt, Whittier; Kenneth Baron, Diamond Bar, all of Calif.

[73] Assignee: Union Oil Company of California, Los Angeles, Calif.

[*] Notice: The portion of the term of this patent subsequent to Aug. 23, 2000 has been disclaimed.

[21] Appl. No.: 679,286

[22] Filed: Dec. 7, 1984

Related U.S. Application Data

[62] Division of Ser. No. 158,981, Jun. 12, 1980, abandoned.

[51] Int. Cl.$^4$ .................................. C10M 105/08
[52] U.S. Cl. .................................. 252/33.6
[58] Field of Search .................. 252/33.6, 46.4, 47, 252/47.5, 49.6; 260/462 R, 429

[56] References Cited

U.S. PATENT DOCUMENTS

| | | | |
|---|---|---|---|
| 2,234,581 | 3/1941 | Rosen | 252/51 |
| 2,441,063 | 5/1948 | Gilmann | 260/462 R |
| 2,999,064 | 9/1961 | Sluham | 252/34.7 |
| 3,000,925 | 9/1961 | Rudner et al. | 260/462 |
| 3,011,880 | 12/1961 | Liao et al. | 44/63 |
| 3,011,881 | 12/1961 | Emrick et al. | 44/63 |
| 3,030,405 | 4/1962 | Rudner et al. | 260/462 |
| 3,185,644 | 5/1965 | Knowles et al. | 252/33.6 |
| 3,186,946 | 6/1965 | Sluhan | 252/49.3 |
| 3,224,971 | 12/1965 | Knowles et al. | 252/46.3 |
| 3,227,739 | 1/1966 | Versteg | 260/462 R |
| 3,232,876 | 2/1966 | Abend | 252/49.6 |
| 3,256,310 | 6/1966 | Weil | 260/462 |
| 3,269,853 | 8/1966 | English et al. | 260/462 R |
| 3,285,855 | 11/1966 | Dexter et al. | 252/57 |
| 3,313,727 | 4/1967 | Peeler | 252/18 |
| 3,321,506 | 5/1967 | Knowles et al. | 252/49.8 |
| 3,429,909 | 2/1969 | Schuster | 260/462 R |
| 3,598,757 | 8/1971 | Cyba | 252/406 |
| 3,598,855 | 8/1971 | Cyba | 260/462 R |
| 3,642,652 | 2/1972 | Birgy | 260/462 R |
| 3,692,681 | 9/1972 | Liston | 252/51.5 A |
| 3,697,574 | 10/1972 | Piasek et al. | 260/462 R |
| 3,755,388 | 8/1973 | Ludwig et al. | 260/404 |
| 3,764,593 | 10/1973 | Schuster | 260/462 R |
| 3,912,643 | 10/1975 | Adams | 252/49.6 |
| 3,912,644 | 10/1975 | Adams | 252/49.6 |
| 3,929,652 | 12/1975 | Seni et al. | 252/46.7 |
| 3,977,986 | 8/1976 | Conte, Jr. et al. | 252/78.3 |
| 4,025,445 | 5/1977 | Hellmuth et al. | 252/49.6 |
| 4,115,286 | 9/1978 | Baldwin et al. | 252/46.3 |
| 4,136,039 | 1/1979 | Jäger | 260/462 R |
| 4,176,076 | 11/1979 | Waldstein | 252/49.6 |
| 4,204,972 | 5/1980 | Knoblauch et al. | 260/462 R |
| 4,226,734 | 10/1980 | Schuster | 252/49.3 |
| 4,382,006 | 5/1983 | Horodysky | 252/49.6 |
| 4,400,284 | 8/1983 | Jessup et al. | 260/462 R |
| 4,406,802 | 9/1983 | Horodysky | 252/49.6 |
| 4,410,436 | 10/1983 | Holstedt et al. | 252/46.4 |
| 4,410,438 | 10/1983 | Horodysky | 252/49.6 |
| 4,412,928 | 11/1983 | Holstedt et al. | 252/46.4 |
| 4,427,560 | 1/1984 | Holstedt et al. | 252/42.7 |
| 4,474,670 | 10/1984 | Braid et al. | 252/32.7 E |
| 4,478,732 | 10/1984 | Horodysky et al. | 252/49.6 |
| 4,490,265 | 12/1985 | Holstedt et al. | 252/47.5 |
| 4,492,640 | 1/1985 | Horodysky et al. | 252/46.3 |
| 4,492,642 | 1/1985 | Horodysky | 252/49.6 |
| 4,511,516 | 4/1985 | Holstedt et al. | 260/462 R |
| 4,533,480 | 8/1985 | Holstedt et al. | 252/46.4 |
| 4,549,975 | 10/1985 | Horodysky | 252/49.6 |
| 4,557,843 | 12/1985 | Holstedt et al. | 252/46.4 |

FOREIGN PATENT DOCUMENTS 1520743 8/1978 United Kingdom .

OTHER PUBLICATIONS

Noller, Chemistry of Organic Compounds W. B. Saunders Co., Phila. p. 827, (1965).
Decision of Board of Patent Appeals and Interferences, U.S. Patent Application Ser. No. 329,385 filed Dec. 10, 1981, by Richard A. Holstedt and Peter Jessup, (Includes newly cited references.)

Primary Examiner—William R. Dixon, Jr.
Assistant Examiner—Margaret B. Medley
Attorney, Agent, or Firm—Dean Sandford; Gregory F. Wirzbicki; Michael C. Schiffer

[57] ABSTRACT

The present invention relates to reaction products derived from boric acid, primary amines, alkene oxides or epoxides and first row transition metals or Group IVA metals, their manufacture and use. These products are used as extreme pressure, anti-wear and friction reducing additives for lubricating oils.

17 Claims, No Drawings

BORON DERIVATIVES

CROSS REFERENCE TO RELATED APPLICATIONS

This is a divisional application of U.S. application Ser. No. 158,981, filed June 12, 1980, now abandoned.

FIELD OF THE INVENTION

This invention relates to new compounds comprising boron and/or metal-boron derivatives and to the preparation of such compounds. These boron and/or metal-boron derivatives are suitable for use as extreme pressure, anti-wear and friction reducing additives for lubricating oils. The compounds herein are conveniently prepared by reacting a boron compound, for example boric acid, with a primary amine, an alkene oxide or epoxide and a transition metal having an atomic number between 21 and 30 or a Group IVA metal of the Periodic Table.

Description of the Prior Art

One method of producing boron derivatives is disclosed in U.S. Pat. No. 2,441,063 to Gilmann which relates to a class of chemical compounds wherein at least one hydroxyl group of an alkanolamine is reacted with a borating agent, e.g. boric acid, to form a boric ester of the alkanolamine, and the resulting product is converted into a salt by reaction with an acid having at least four carbon atoms. The compounds thus formed are said to be useful as wetting agents and detergents.

U.S. Pat. No. 3,227,739 to Versteeg discloses anti-rust additives which are prepared by reacting a dialkanolamine and a long-chain, 1,2 epoxide under a nitrogen atmosphere at increased temperature. The resulting product is reacted with boric acid to prepare the anti-rust additives. The additives are said to improve the anti-rust properties of lubricating oils.

U.S. Pat. No. 3,321,506 to Knowles et al. discloses organo-boron compounds such as borate esters used as lubricating oil additives. The organo-boron compounds are prepared by the reaction of a hydroxy substituted amine with a trialkyl or aryl borate to form substituted amine salts of boron acids. The compounds are described as useful as load carrying additives for mineral and synthetic base lubricating oils.

Cyclic borates are disclosed in U.S. Pat. No. 3,598,855 to Cyba, which relates to cyclic borates of polymeric alkanolamines formed by reacting a borylating agent, for example boric acid, with a polymeric alkanolamine. The polymeric alkanolamine is derived from the reaction product of a suitable amine with an epihalohydrin compound, for example epichlorohydrin. The cyclic borates are used as additives in organic substances to inhibit deterioration due to oxidation, weathering, heat or other undesired reactions.

Another boron derivative is disclosed in U.S. Pat. No. 4,136,039 to Jager which relates to compounds derived from the reaction product of boric acid and an amine, for example, an N-substituted bis 2,3-dihydroxy-propylamine. The boron compounds thus produced are said to be useful as brightening agents, anti-soil redeposition agents, surface active agents and emulsifiers or dispersing agents.

From the foregoing, it can readily be determined that there is an ongoing search for boron compounds and derivatives which are suitable for use as lubricating oil additives as well as for other industrial purposes.

SUMMARY OF THE INVENTION

The present invention relates to novel boron or metal-boron derivates of the formula:

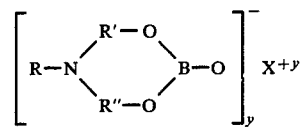

wherein R is hydrogen, alkyl, cyclic, alicyclic, aryl, alkylaryl, or arylalkyl radicals having from about 1 to about 24 carbon atoms, R' and R" are either straight or branched carbon chains, cyclic, alicyclic, aryl, alkylaryl or arylalkyl radicals having from about 2 to about 20 carbon atoms, y is an integer of 1 to 4, and X is either hydrogen or a metal selected from a transition metal having an atomic number from 21 to 30 or a group IV A metal of the Periodic Table.

The novel boron or metal-boron derivatives are produced by (A) reacting a primary amine with an epoxide having from about 2 to about 20 carbon atoms to form a reaction product, (B) reacting the product of step (A) with boric acid to form a boramid. The boramid thus formed is reacted with a transition metal or salt thereof having an atomic number from 21 to 30 or a Group IVA metal of the Periodic Table or salt thereof to produce a metal-boron derivative or metal-boramid compound.

DESCRIPTION OF THE INVENTION

The present invention resides in novel boron or metal-boron derivatives, their use and manufacture. The novel boron compounds of the present invention, including metal derivatives thereof are referred to herein as boramids or metal-boramids. The above compounds are conveniently prepared by reacting a primary amine with an alkene oxide or epoxide and boric acid to produce the boramid compound, and reacting the compound thus produced with a transition or Group IVA metal to produce the metal derivative thereof.

The primary amines used herein may conveniently be derived from a commercial source or may be produced from alkyl, cyclic, alicyclic, aryl, alkylaryl or arylalkyl halides and ammonia using conventional techniques and apparatus. These halides react with ammonia at moderately high temperatures and under pressure to give a mixture of primary, secondary and tertiary amines. The primary amine yield of this process may be improved by using an excess of ammonia in the reaction.

Another typical process for producing amines consists of reacting alcohols with ammonia in the vapor phase at temperatures of from 570° F. to 940° F. under 200 to 1,000 p.s.i.g. For the lower molecular weight alcohols, temperatures of 750° F., pressures of about 200 p.s.i.g. and a reaction time of 2 to 3 hours are desirable. A mixture of primary, secondary and tertiary amines is formed wherein the amines exist in equilibrium with each other. It is possible to improve the yield of the desired amine by recycling undesired amines through the vapor phase. The most convenient method of obtaining the desired primary amine is through commercial sources.

Primary amines which are suitable for use herein include methyl amine, ethylamine, propylamine, butylamine, octodecyl amine, cyclohexylamine, dodecylamine, phenylamine, oleylamine, cocoamine and tallowamine and mixtures thereof.

The alkene oxides or epoxides which are suitable for use herein may be prepared by three general methods (1) direct oxidation of olefins in the presence of a conventional oxidation catalyst; (2) reaction of olefins with peroxy acids; and (3) hydrolysis of chlorohydrins with bases. Chlorohydrins are produced by a two step reaction wherein an alkene oxide, chlorine and water are passed into a packed reactor to form the respective alkylene chlorohydrin, for example ethylene chlorohydrin.

Another convenient method for preparing alkene oxides or epoxides involves vapor phase oxidation of olefins. For example, an olefin and oxygen or air are passed over a silver oxide catalyst supported on alumina in the vapor phase under increased temperature and pressure to produce an epoxide.

A wide variety of alkene oxides or epoxides may be used to prepare the precursor for the boramid compounds herein. Typical alkene oxides or epoxides which are suitable for use include ethylene oxide, propylene oxide, 1,2-epoxybutane, cyclohexene oxide, cyclooctene oxide, cyclododecene oxide, and 1,2-epoxybenzene and mixtures thereof.

The boramid and/or metal boramid compounds herein are conveniently prepared by reacting boric acid with a dialkoxylated primary amine having a carbon chain containing from about 1 to about 24 carbon atoms, especially from about 1 to about 18 carbon atoms. The primary amine is alkoxylated with an alkene oxide or epoxide having straight or branched carbon chains, cyclic, alicyclic, aryl, alkyaryl or arylalkyl radicals containing from about 2 to about 20 carbon atoms, especially from about 2 to about 10 carbon atoms.

Generally, the primary amine is reacted with an alkene oxide or epoxide in the presence of a solvent for example toluene, methanol or water to produce a dialkoxylated amine. The primary amine and alkene oxide or epoxide are reacted at a molar weight ratio 1:2. The solvent is added in sufficient quantity to solubilize or disperse the reactants to ensure better contact of said reactants. After the reaction proceeds to completion, the solvent is removed from the reaction product using convention techniques and apparatus, for example, by evaporation, distillation, etc.

Next, the dialkoxylated amine is reacted with boric acid at a molar ratio of from about 1:2 to about 1:1 in the presence of a solvent, for example, xylenes, benzene, toluene, etc. to produce a boramid compound. Normally, the solvent will comprise from about 20 to about 50 weight percent, especially from about 30 to about 40 weight percent of the reaction mixture. The boramid compound thus produced will contain from about 0.5 to about 10 weight percent, preferably from about 2 to about 5 weight percent of boron. The reactions herein are conducted under reflux using standard equipment at a temperature of from about 176° F. to about 450° F., especially from about 176° F. to about 300° F., at atmospheric pressure for about 1 to about 5 hours.

Preferred boramid compounds produced in accordance with the procedure herein are selected from the group comprising methylaminodiethylate hydrogen borate, ethylaminodiethylate hydrogen borate, propylaminodiethylate hydrogen borate, butylaminodiethylate hydrogen borate, octadecylaminodiethylate hydrogen borate, dodecylaminodiethylate hydrogen borate, cyclohexylaminodiethylate hydrogen borate, phenylaminodiethylate hydrogen borate, oleylaminodiethylate hydrogen borate, cocoaminodiethylate hydrogen borate, tallowaminodiethylate hydrogen borate, dodecylamino di(-2-methylethylate)hydrogen borate, and dodecylamino di(-2-phenylethylate)hydrogen borate and mixtures thereof.

Metals are conveniently incorporated into the boramid compounds herein using conventional methods and apparatus. Generally, the metal is reacted with the desired boramid compound in salt form. Thus, the metal acetates, propionates, etc. are suitable for use. It should be noted that not all metal salts are desirable for incorporating the metal ion into the boramid compound. The metal carbonates, nitrates, chlorides and sulfates to name a few, are all undesirable as vehicles for imparting metal ions into the boramid compound. These metal salts experience solubility problems, separation problems and in addition, undesirable ions are frequently left in the boramid compound. Generally, the boramid compounds are reacted with the metal compounds herein in a molar ratio range of from about 1:4 to about 6:1, especially from about 1:1 to about 4:1.

Desirable metals are conveniently selected from transition metals having an atomic number from 21 to 30 or Group IVA metals of the Periodic Table. Transition metals which are suitable for use are selected from scandium, titanium, vanadium, chromium, manganese, iron, cobalt, nickel, copper and zinc and mixtures thereof. Suitable Group IVA metals include lead and tin and mixtures thereof. Normally, the metal will comprise from about 1 to about 17 weight percent, preferably from about 5 to about 9 weight percent of the boramid compound.

When a metal is incorporated into the boramid compounds herein, the metal will add to the hydroxy component of the structure. In addition, the Examples hereinafter recite cocoaminodiethylate hydrogen borate as boramid C/12, tallowaminodiethylate hydrogen borate as boramid T/12 and octadecylaminodiethylate hydrogen borate as boramid 18/12. The corresponding metal-boron derivative will, of course, recite the desired metal in the boramid nomenclature, for example, zinc boramid C/12, etc.

The invention will be further described with reference to the following Examples.

EXAMPLE I

A boramid compound is prepared by adding 20 grams of boric acid, 95 grams of Armak Ethomeen C/12 [bis(2-hydroxyethyl)cocoamine] and 250 ml of toluene to a single-necked one liter round-bottomed flask. The toluene acts as a solvent and as an azeotrope for water produced during the reaction. It should be noted that boric acid is not soluble in toluene or Ethomeen C/12. The flask is placed in a heating mantle and fitted with a Dean-Stark trap that is topped with a condenser. The mixture thus formed is heated until it begins to reflux. Next, the mantle is adjusted to give a moderate reflux rate. The reaction mixture is refluxed for one hour, or until the stoichiometric amount of water (12 ml.) collects in the Dean-Stark trap and all of the boric acid has dissolved, after which the toluene is distilled from the reaction product. The reaction product (103 grams) is designated boramid C/12 and has a clear golden color. Boramid C/12 is a fluid liquid while hot but sets into a soft viscous material when cooled to room temperature. The compound is readily soluble in hydrocarbon solvents and water.

EXAMPLE II

A boramid compound is prepared by following the procedure of Example I with the following substitution: Armak Ethomeen T/12 [bis(2-hydroxyethyl)tallowamine] is substituted for the Armak Ethomeen C/12. Substantially the same results are obtained, however, the resulting compound is designated boramid T/12.

EXAMPLE III

A boramid compound is prepared by mixing 20 grams of boric acid, 95 grams of Armak Ethomeen 18/12 [bis(2-hydroxyethyl)octadecylamine] and, as a solvent, 250 ml of toluene in a single-necked one liter round-bottomed flask. The flask is placed in a heating mantle and fitted with a Dean-Stark trap and water cooled condenser. The mixture is heated under reflux for one hour, during which 12 ml of water collects in the Dean-Stark trap. The toluene is then distilled from the reaction product. The compound is designated boramid 18/12 and is readily soluble in hydrocarbon solvents and water.

EXAMPLE IV

The procedure of Example III is followed to prepare a boramid compound with the following exception: N,N-diethanol-n-methylamine (46.3 grams) is substituted for the Armak Ethomeen 18/12. The reaction product thus produced is a liquid product with the consistency of honey when hot and becomes a waxy semi-solid when cooled to room temperature.

EXAMPLE V

Boric acid (20 grams), N,N-diethanol-N-phenylamine (46.3 grams) and 250 mls of toluene are mixed in a one liter single-necked flask to prepare a boramid compound. The flask is equipped with a heating mantle, Dean-Stark trap and water-cooled condenser. The mixture is heated under reflux until the reaction is completed (12 ml of water collects), approximately one hour, and the toluene is distilled from the reaction mixture. The product thus prepared is suitable for use as an extreme pressure, antiwear and friction reducing additive for lubrication compositions.

EXAMPLE VI

A metal derivative of boramid C/12 is prepared by mixing 54 grams of the product of Example I (boramid C/12), 400 ml of toluene, 24.6 grams of nickel acetate and 150 ml of methanol in a single-necked, one liter round bottom flask which is equipped with a heating mantle and water-cooled condenser. The mixture is refluxed for four hours. Next, water, toluene, methanol and acetic acid are distilled from the reaction product. The product (59 grams) contained 7.8 weight percent nickel as determined by emission spectroscopy, the resulting product is a fluid green liquid when hot, which turns into a solid upon cooling to room temperature. The product is readily soluble in hydrocarbon solvents and water.

EXAMPLE VII

A metal boramid is prepared by following the procedure of Example II with the following exception: the boramid T/12 (54 grams), 400 ml of toluene, 24 grams of nickel acetate and 150 mls of methanol are mixed in a single-necked, one liter round bottom flask, equipped with a heating mantle, Dean-Stark trap and water-cooled condenser. The mixture is refluxed for four hours and the toluene, water and acetic acid are distilled from the reaction product.

EXAMPLE VIII

A zinc derivative of boramid C/12 is prepared by mixing 54 grams of the reaction product of Example I (boramid C/12) with 400 ml of toluene, 19.1 grams of zinc acetate and 50 ml of methanol in a single-necked, one liter round bottom flask, equipped with a heting mantle and water-cooled condenser. The mixture is refluxed for four hours and the toluene, methanol, water and acetic acid are distilled. The resulting product is suitable for use as an extreme pressure, anti-wear, friction reducing additive for lubricating compositions.

EXAMPLE IX

A metal boramid is prepared by following the procedure of Example VII with the following exception: zinc acetate is substituted for the nickel acetate to produce zinc-boramid T/12.

It is to be noted that transition metals having an atomic number from 21 to 30, and Group IVA metals of the Periodic Table may be substituted for the nickel and zinc metals herein to prepare corresponding metal boramids.

EXAMPLE X

A metal-boramid is prepared by following the procedure of Example VI with the following changes: 31 grams of boramid C/12 is mixed with 19 grams of lead (II) acetate, 150 ml. of toluene and 25 ml of methanol. The mixture is refluxed for 2 hours, after which, the toluene, methanol, water and acetic acid (produced acetate) are distilled using conventional techniques and apparatus. The resulting lead-boramid C/12 product (32.6 grams) is a golden colored oily liquid with the consistency of honey.

EXAMPLE XI

A copper boramid is prepared by adding 62 grams of boramid C/12, 150 ml of toluene, 50 ml of water and 18.2 grams of cupric acetate to a 500 ml., single necked round bottom flask equipped with a Dean-Stark trap and condenser. The mixture is refluxed for 8 hours, after which, water, toluene and produced acetic acid (from acetate) are distilled leaving 68 grams of a green solid.

EXAMPLE XII

A lubricant composition containing nickel-boramid C/12 and 450 neutral oil is tested for anti-wear and properties in a 1973 Chevrolet 350 cu. in. displacement V-8 engine which is run continuously for 196 hours on a single fill of the lubricating composition. The lubricating oil does not contain conventional zinc dialkydithiophosphate anti-wear additives. The lubricant composition is disclosed in detail in Table 4 below.

TABLE 4

| Compound | Weight Percent |
|---|---|
| 450 neutral oil | 89.965 |
| Boramid C/12 | 2.5.000 |
| Nickel-boramid C/12 | 2.5.000 |
| Oronite OLOA 1200[A] | 4.000 |
| Chlorowax 40[B] | 1.000 |
| UNAD 242[C] | 0.010 |
| Terphthalic Acid[D] | 0.005 |

TABLE 4-continued

| Compound | Weight Percent |
|---|---|
| Quinizarin[E] | 0.020 |

[A]Oronite OLOA 1200 — alkyl succinimide type ashless dispersant.
[B]Chlorowax 40 — Chlorided paraffin containing 40% chlorine.
[C]UNAD 242 — Silicone type defoamant containing kerosene.
[D]Terphthalic acid — Corrosion inhibitor.
[E]Quinizarin — Antioxidant.

The Chevrolet engine is programed to run in a repeating cycle that averaged approximately 40 MPH. The cycle is disclosed in Table 1 below.

TABLE 1

| Cycle | RPM | Speed (MPH) | Time (MIN.) |
|---|---|---|---|
| 1 | 700 | 0 | 2.0 |
| 2 | 1700 | 45 | 3.0 |
| 3 | 1200 | 30 | 4.0 |
| 4 | 2225 | 60 | 7/60 |
| 5 | 2400 | 65 | 3.0 |

After the 196 hour engine test is completed, several areas in the engine which are subject to wear are closely examined. These areas include: main bearings, top end bearings, cam shaft bearings, valve lifters and cham shaft lobes.

The length of the engine run is equivalent to approximately 8,000 miles of driving. A detailed examination of the above-described components indicates no abnormal or excessive wear.

EXAMPLE XIII

The extreme pressure, anti-wear and friction reducing additives boramid C/12 produced in Example I and boramid T/12 produced in Example II are mixed with separate portions of SAE 10W/40 motor oil[a] containing 0.15 weight percent of phosphorous and 0.17 weight percent of zinc. In addition, the motor oil contains 0.21 weight percent of calcium.

Each lubricant composition is tested in accordance with the procedure disclosed in ASTM D3233-73 (Reapproved 1978) using a Falex lubricant tester. The test, in accordance with the above ASTM designation, is performed by applying resistance to a revolving metal journal. A rachet mechanism movably attached to two V-Blocks applies resistance by steadily increasing pressure on the journal. The metal journal and V-Blocks (steel) are submerged in the lubricant composition to be tested. The results are indicated in Table 2 below.

TABLE 2

| | Torque on Journal (lbs.-in.) | | |
|---|---|---|---|
| True Load lbs | SAE 10W/40[a] Without Boramid Additive | SAE 10W/40 With 1% Boramid C-12 | SAE 10W/40 With 1% Boramid T-12 |
| 100 | 8 | 7½ | 7½ |
| 250 | 12 | 10 | 9 |
| 500 | 19 | 15 | 14 |
| 750 | 22 | 18 | 19 |
| 1,000 | 25 | 22 | 22 |
| 1,250 | 35 | 25 | 25 |
| 1,500 | Journal | 27 | 27 |
| 1,750 | — | Journal Shear | 33 |
| 2,250 | — | — | Journal Shear |

[a]Union Super Motor Oil, marketed commercially by the Union Oil Company of California.

EXAMPLE XIV

The extreme pressure, anti-wear and friction reducing additive, lead boramid C/12 produced in accordance with the procedure of Example XVII is blended with 450 neutral oil at 5 percent by weight based on the total weight of the lubricant composition. This lubricant composition is compared to Arco graphite lubricant and ASTM high reference oil, SAE 20W-30 for friction reduction and extreme pressure properties:

The lead boramid C/12 and 450 neutral oil mixture is compared to Arco graphite and ASTM, SAE 20W-30 in accordance with the procedure disclosed in ASTM:D3233-73 (Reapproved 1978) using a Falex Lubricant tester. The test is performed by applying resistance to a revolving metal journal. Resistance is applied by two V-Blocks equipped with a ratchet mechanism which steadily increases pressure on the journal. The metal journal and V-Blocks are composed of steel in this example. The metal journal and V-Blocks are submerged in the lubricating composition to be tested. The results are indicated in Table 3 below.

TABLE 3

| | Torque on Journal (lbs.-in.) | | |
|---|---|---|---|
| True Load (lbs) | 450 Neutral Oil with Lead-Boramid C/12 | Arco Graphite | ASTM SAE 20W-30 |
| 300 | 7 | 6 | 6 |
| 500 | 11 | 8 | 7 |
| 750 | 14 | 16 | 12 |
| 1000 | 20 | 21 | 20 |
| 1250 | 23 | 26 | 24 |
| 1500 | 40 | Journal Shear | Journal Shear |
| 1750 | 85 | | |
| 2000 | 94 | | |
| 2250 | 90 | | |
| 2500 | 71 | | |
| 2750 | 79 | | |
| 3000 | 70 | | |
| 3250 | 70 | | |

Stopped due to inability to increase load.

We claim:
1. A compound having the formula:

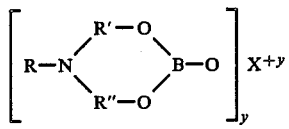

wherein R is an aryl, alkyl, alkylaryl or arylalkyl radical having 1 to about 24 carbon atoms, R' and R" are independently selected from the group consisting of aryl, alkylaryl or arylalkyl radicals having from about 6 to about 20 carbon atoms, y is an integer of 1 to 4, and X is a metal selected from the group consisting of transition metals having an atomic number from 21 to 30, Group IVA metals and mixtures thereof.

2. The compound of claim 1 wherein R is an aryl, alkyl, alkylaryl or arylalkyl radical having from 9 to about 24 carbon atoms.

3. The compound of claim 1 wherein R' and R" are independently selected from the group consisting of aryl, alkylaryl or arylalkyl radicals having from about 2 to about 10 carbon atoms.

4. The compound of claim 1 wherein X is scandium, titanium, vanadium, chromium, manganese, iron, cobalt, nickel, copper, zinc, tin, lead and mixtures thereof.

5. The compound of claim 1 wherein said compound is comprised of from about 1 to about 17 weight percent of a metal.

6. The compound of claim 1 wherein R is an aryl, alkyl, alkylaryl or arylalkyl radical having from 9 to about 18 carbon atoms.

7. A compound comprising the reaction product of: (A) a borate selected from the group consisting of octadecylaminodiethylate hydrogen borate, dodecylaminodiethylate hydrogen borate, cyclohexylaminodiethylate hydrogen borate, phenylaminodiethylate hydrogen borate, oleylaminodiethylate hydrogen borate, cocoaminodiethylate hydrogen borate, dodecylamino(di-2-methylethylate)hydrogen borate and dodecylamino(di-2-phenylethylate)hydrogen borate and mixtures thereof; and (B) a metal selected from the group consisting of scandium, titanium, vanadium, chromium, manganese, iron, cobalt, nickel, copper, zinc, tin, lead and mixtures thereof.

8. A compound comprising the reaction product of: (A) a borate selected from the group consisting of methylaminophenylaminodiethylate hydrogen borate, octadecylaminodiethylate hydrogen borate, cocoaminodiethylate hydrogen borate and tallowaminodiethylate hydrogen borate and mixtures thereof; and (B) a metal selected from the group consisting of nickel, zinc, copper and lead the mixtures thereof.

9. A process comprising: (1) reacting a primary amine with an alkene oxide or epoxide to produce a dialkoxylated amine; (2) reacting the dialkoxylated amine with boric acid to produce a boron-containing compound; and (3) reacting with boron-containing compound with a metal selected from the group consisting of transition metals having an atomic number from 21 to 30, Group IV-A metals and mixtures thereof.

10. The process according to claim 9, wherein the metal is selected from scandium, titanium, vanadium chromium, manganese, iron, cobalt, nickel, copper, zinc, tin and lead and mixtures thereof.

11. The process according to claim 1 wherein the boron-containing compound and metal are contacted at a molar ratio of from about 1:4 to about 6:1.

12. The process of claim 9 wherein the reacting steps (1), (2) and (3) are carried out at a temperature of from about 176° F. to about 450° F., at atmospheric pressure and over a time period of from about 1 hour to about 5 hours.

13. A process comprising: (1) reacting a primary amine with an alkene oxide or epoxide at a molar ratio of 1:2 to produce a dialkoxylated amine; (2) reacting the dialkoxylated amine with boric acid at a molar ratio of from 1:2 to about 1:1 to produce a boron-containing compound, and (3) reacting the boron-containing compound with a metal selected from the group consisting of transition metals having an atomic number from 21 to 30, Group IV-A metals and mixtures thereof, wherein said boron-containing compound and metal are reacted at a molar ratio from about 1:1 to about 4:1.

14. The process according to claim 13 wherein the metal is selected from the group consisting of scandium, titanium, vanadium, chromium, manganese, iron, cobalt, nickel, copper, zinc, tin and lead and mixtures thereof.

15. The process according to claim 13 where the reacting steps (1), (2) and (3) are carried out at a temperature of from about 176° F. to about 450° F., atmospheric pressure and over a time period of from about 1 hour to about 5 hours.

16. A process comprising: (1) reacting a primary amine selected from the group consisting of methylamine, phenylamine, octadecylamine, cocoamine and tallowamine and mixtures thereof, with ethylene oxide at a molar ratio of 1:2 to produce a dialkoxylated amine; (2) reacting the dialkoxylated amine with boric acid at a molar ratio of from about 1:2 to about 1:1 to produce a boron-containing compound; and (3) reacting the boron-containing compound with a metal selected from the group consisting of nickel, zinc, copper, lead and mixtures thereof at a molar ratio of from about 1:1 to about 4:1.

17. The process of claim 16 wherein the reacting steps (1), (2) and (3) are carried out at a temperature of from about 176° F. to about 450° F., atmospheric pressure and over a time period of from about 1 hour to about 5 hours.

* * * * *